United States Patent
Im et al.

(10) Patent No.: US 11,607,671 B2
(45) Date of Patent: Mar. 21, 2023

(54) ALKALI METAL AND/OR ALKALINE EARTH METAL-DOPED TRANSITION METAL-HYDROGEN ACTIVE METAL COMPOSITE OXIDE CATALYST AND PROCESS FOR PREPARING BUTADIENE USING THE SAME

(71) Applicants: SK Innovation Co., Ltd., Seoul (KR); SK Geo Centric Co., Ltd., Seoul (KR)

(72) Inventors: Ju Hwan Im, Daejeon (KR); Hee Soo Kim, Daejeon (KR); Ho Won Lee, Daejeon (KR)

(73) Assignees: SK Innovation Co., Ltd., Seoul (KR); SK Geo Centric Co., Ltd., Seoul (KR)

( * ) Notice: Subject to any disclaimer, the term of this patent is extended or adjusted under 35 U.S.C. 154(b) by 0 days.

(21) Appl. No.: 17/224,282

(22) Filed: Apr. 7, 2021

(65) Prior Publication Data

US 2021/0316277 A1   Oct. 14, 2021

(30) Foreign Application Priority Data

Apr. 10, 2020   (KR) .................. 10-2020-0044232

(51) Int. Cl.
| | |
|---|---|
| *B01J 23/42* | (2006.01) |
| *B01J 21/04* | (2006.01) |
| *B01J 23/10* | (2006.01) |
| *B01J 37/08* | (2006.01) |
| *C07C 5/32* | (2006.01) |

(Continued)

(52) U.S. Cl.
CPC ............... *B01J 23/42* (2013.01); *B01J 21/04* (2013.01); *B01J 23/002* (2013.01); *B01J 23/10* (2013.01); *B01J 23/38* (2013.01); *B01J 23/70* (2013.01); *B01J 35/0046* (2013.01); *B01J 35/0086* (2013.01); *B01J 37/04* (2013.01);

(Continued)

(58) Field of Classification Search
CPC . B01J 23/42; B01J 23/002; B01J 23/10; B01J 23/38; B01J 23/70; B01J 21/04; B01J 35/0046; B01J 35/0086; B01J 37/04; B01J 37/08; B01J 37/16; C07C 5/325
USPC .................. 502/305–355; 585/616, 654, 663
See application file for complete search history.

(56) References Cited

U.S. PATENT DOCUMENTS

| | | | | |
|---|---|---|---|---|
| 4,374,046 A | * | 2/1983 | Antos | ..................... C07C 5/367 585/444 |
| 10,307,737 B2 | | 6/2019 | Kim et al. | |

(Continued)

FOREIGN PATENT DOCUMENTS

| | | |
|---|---|---|
| WO | 2013098761 A2 | 7/2013 |
| WO | 2019147424 A1 | 8/2019 |

OTHER PUBLICATIONS

Im et al., "Physicochemical Stabilization of Pt against Sintering for a Dehydrogenation Catalyst with High Activity, Selectivity, and Durability", ACS Catalysis, pubs.acs.org/acscatalysis, 2016, pp. 2819-2826, vol. 6.

(Continued)

*Primary Examiner* — Patricia L. Hailey
(74) *Attorney, Agent, or Firm* — The Webb Law Firm (57) ABSTRACT

In the present disclosure, a composite oxide catalyst capable of effectively suppressing side reactions at the time of dehydrogenation of C4 hydrocarbons having single bonds or one double bond and a process for preparing butadiene, in particular 1,3-butadiene, with a high selectivity and a high yield using the same are described.

19 Claims, 1 Drawing Sheet

(51) Int. Cl.
- *B01J 23/00* (2006.01)
- *B01J 23/38* (2006.01)
- *B01J 23/70* (2006.01)
- *B01J 35/00* (2006.01)
- *B01J 37/04* (2006.01)
- *B01J 37/16* (2006.01)

(52) U.S. Cl.
CPC .............. *B01J 37/08* (2013.01); *B01J 37/16* (2013.01); *C07C 5/325* (2013.01)

(56) References Cited

U.S. PATENT DOCUMENTS

| | | |
|---|---|---|
| 10,486,140 B2 | 11/2019 | Iezzi et al. |
| 2004/0133054 A1* | 7/2004 | Pelati ........................ B01J 23/80 502/316 |
| 2010/0010280 A1* | 1/2010 | Fridman ................ B01J 35/023 502/308 |
| 2013/0178682 A1 | 7/2013 | Luo et al. |
| 2017/0120222 A1 | 5/2017 | Kim et al. |

OTHER PUBLICATIONS

Sattler et al., "Platinum-Promoted Ga/Al2O3 as Highly Active, Selective, and Stable Catalyst for the Dehydrogenation of Propane", Angewandte Chemie, Wiley Online Library, 2014, pp. 9405-9410, vol. 126, Verçffentlicht von Wiley-VCH Verlag GmbH & Co. KGaA, Weinheim.

* cited by examiner

ALKALI METAL AND/OR ALKALINE EARTH METAL-DOPED TRANSITION METAL-HYDROGEN ACTIVE METAL COMPOSITE OXIDE CATALYST AND PROCESS FOR PREPARING BUTADIENE USING THE SAME

CROSS-REFERENCE TO RELATED APPLICATION

This application claims priority to Korean Patent Application No. 10-2020-0044232 filed Apr. 10, 2020, the disclosure of which is hereby incorporated by reference in its entirety.

BACKGROUND OF THE INVENTION

Field of the Invention

The present disclosure relates to an alkali metal and/or an alkaline earth metal-doped transition metal-hydrogen active metal composite oxide catalyst and a process for preparing butadiene using the same. More specifically, the present disclosure relates to a composite oxide catalyst capable of effectively suppressing side reactions during dehydrogenation of C4 hydrocarbons having single bonds or one double bond and a process for preparing butadiene, in particular 1,3-butadiene, with a high selectivity and a high yield using the same.

Description of the Related Art

Recently, as the production of shale gas containing a large amount of gases such as methane and ethane has rapidly increased, the capacity utilization of ethane crackers has been greatly increased compared with naphtha crackers, in order to improve the economic efficiency. As a result, production of olefins such as propylene, butylene, and butadiene that have been produced as by-products of naphtha crackers has decreased. Hence, studies on a dehydrogenation process for directly producing such olefins from propane, butane and the like having a short carbon length are in progress.

Butadiene is a key raw material for the production of synthetic rubber and is in constant demand around the world. For example, butadiene is used in the production of synthetic rubbers such as butadiene homopolymer, styrene-butadiene-rubber, nitrile-rubber and thermoplastic ternary interpolymers such as acrylonitrile-butadiene-styrene copolymer (ABS).

Currently, butadiene produced as a by-product of naphtha cracking accounts for about 95% of the total production thereof, but the low yield of butadiene, in particular 1,3-butadiene, has been pointed out as a problem since various hydrocarbons, for example, methane, ethane, ethene, acetylene, propane, propylene, C5 and higher hydrocarbon mixtures are generated in addition to butadiene. As described above, it is difficult to meet the increasing demand for butadiene and there are limitations in properly dealing with fluctuations in market demand by the process of producing butadiene through naphtha cracking. In this situation, a number of studies have recently been conducted to directly produce butadiene from butane through oxidative or non-oxidative dehydrogenation.

Among the above studies, the oxidative dehydrogenation (Oxo-D, UOP) process has an advantage that the thermodynamic marginal yield of butadiene can be increased by consuming hydrogen generated in the reaction as water but has a disadvantage that steam should be needed for the reaction and the post-separation steps becomes complicated. On the other hand, the non-oxidative dehydrogenation (Catadiene, Lummus) process has an advantage that the generation of oxygen and various oxides can be suppressed but requires a low reaction pressure and a high reaction temperature in order to increase the thermodynamic marginal yield for the production of butadiene. In particular, the catalyst may be irreversibly deactivated under high temperature reaction and regeneration conditions.

In this regard, literatures have been reported in which a catalyst containing gallium and platinum supported on alumina is used in order to overcome the limitations of dehydrogenation catalyst (JJHB Sattler et al., Angew. Chem., 126:9405, 2014 and US Patent Publication No. 2013/0178682). A technology capable of effectively suppressing the sintering of platinum by subjecting gallium, platinum, cerium, and alumina to one-pot synthesis has also been reported as a method of improving the regeneration stability of catalyst (J. Im, ACS Catal., 6:2819, 2016 and US Patent Publication No. 10,307,737). In the prior arts described above, it is disclosed that those technologies can be applied to various dehydrogenations, but the prior arts mainly focus on the production of propylene through the dehydrogenation of propane and the production of isobutylene (having one double bond) through the dehydrogenation of isobutane (see Examples and the like).

However, in the case of the dehydrogenation to produce butadiene, in particular 1,3-butadiene (having two double bonds) from butane, the probability of occurrence of side reactions such as an isomerization reaction and/or a cracking reaction increases as compared to the dehydrogenation of propane. Hence, it is required to control the acid sites of catalyst and platinum activity in the case of attempting to synthesize butadiene with a high yield.

SUMMARY OF THE INVENTION

In an embodiment according to the present disclosure, it is intended to provide a method of achieving a high selectivity and a high yield of butadiene during dehydrogenation of C4 hydrocarbons without deteriorating the catalytic activity by controlling the acid sites in the dehydrogenation catalyst used in the process for producing butadiene from a feedstock containing butane and suppressing side reactions such as isomerization and/or cracking reactions.

According to a first aspect of the present disclosure, there is provided a dehydrogenation catalyst for butadiene preparation, which comprises:

at least one first transition metal selected from the group consisting of gallium, vanadium, chromium, manganese, molybdenum, and zinc;

at least one hydrogen active metal selected from the group consisting of elements belonging to groups 8, 9, 10, and 11 of the periodic table;

at least one doping metal selected from the group consisting of elements belonging to groups 1 and 2 of the periodic table; and alumina, wherein a content of the first transition metal is determined in a range of 0.1% to 20% by weight based on a weight of alumina, a content of the hydrogen active metal is determined at 0.1% by weight or less based on a weight of alumina, a content of the doping metal is determined in a range of 0.01% to 5% by weight based on a weight of alumina, and the first transition metal and the doping metal are each contained in alumina in a solid solution form and the hydrogen active metal is surrounded by alumina containing the first transition metal and doping metal.

In an exemplary embodiment, the dehydrogenation catalyst may further comprise at least one second transition metal selected from the group consisting of cerium and zirconium, wherein a content of the second transition metal may be determined in a range of 0.1% to 20% by weight based on a weight of alumina and the second transition metal may be in a form of being loaded on alumina.

According to a second aspect of the present disclosure, there is provided a process for preparing a dehydrogenation catalyst for butadiene preparation, which comprises:

providing a precursor of at least one first transition metal selected from the group consisting of gallium, vanadium, chromium, manganese, molybdenum, and zinc;

providing a precursor of at least one hydrogen active metal selected from the group consisting of elements belonging to groups 8, 9, 10, and 11 of the periodic table;

providing a precursor of at least one doping metal selected from the group consisting of elements belonging to groups 1 and 2 of the periodic table; and providing a precursor of alumina;

mixing the precursor of first transition metal, the precursor of hydrogen active metal, the precursor of doping metal, and the precursor of alumina in one pot to form a one-pot precursor mixture; and reacting the one-pot precursor mixture by a sol-gel method to synthesize a catalyst, wherein a content of the first transition metal is determined in a range of 0.1% to 20% by weight based on a weight of alumina, a content of the hydrogen active metal is determined at 0.1% by weight or less based on a weight of alumina, a content of the doping metal is determined in a range of 0.01% to 5% by weight based on a weight of alumina, and the first transition metal and the doping metal are each contained in alumina in a solid solution form and the hydrogen active metal is surrounded by alumina containing the first transition metal and doping metal.

In an exemplary embodiment, the process may further comprise mixing a precursor of at least one second transition metal selected from the group consisting of cerium and zirconium in the one pot, wherein a content of the second transition metal may be determined in a range of 0.1% to 20% by weight based on a weight of alumina in the dehydrogenation catalyst.

In an exemplary embodiment, the process may further comprise drying the synthesized catalyst, followed by subjecting to heat treatment after performing the step of synthesizing a catalyst by a sol-gel method.

According to a third aspect of the present disclosure, there is provided a process for preparing butadiene, which comprises:

providing a feedstock containing C4 hydrocarbons having a single bond or one double bond;

subjecting the C4 hydrocarbons in the feedstock to dehydrogenation in presence of the afore-mentioned catalyst to form a product containing butadiene in an increased content; and recovering butadiene from the product.

DESCRIPTION OF THE INVENTION

The present invention can all be achieved by the following description. The following description should be understood as describing a preferred embodiment of the present invention, and the present invention is not necessarily limited thereto. In addition, it should be understood that the accompanying drawings are provided to aid the understanding, and the present invention is not limited thereto.

Terms used in the present specification may be defined as follows.

A "heterogeneous catalyst" may refer to a catalyst that exists in a phase different from that of the reactant in the course of the catalytic reaction and may mean, for example, a catalyst that does not dissolve in the reaction medium. In the case of a heterogeneous catalyst, at least one reactant is required to be diffused and adsorbed to the surface of the heterogeneous catalyst in order to cause the reaction, and the product is required to be desorbed from the surface of the heterogeneous catalyst after the reaction.

A "support" may mean a material (typically a solid material) having a high specific surface area to which the catalytically active component is attached and may or may not participate in the catalytic reaction.

A "hydrogen active metal" may mean a metal capable of forming hydrogen activated by contact with molecular hydrogen, specifically, dissociated hydrogen in a broad sense.

The term "crystalline" or "crystalloid" may typically mean an arbitrary solid material that is ordered such that the atoms have a lattice structure (for example, three-dimensional order), and the crystallinity can be generally identified by X-ray diffraction analysis (XRD), nuclear magnetic resonance analysis (NMR), differential scanning calorimetry (DSC), or combination thereof. The term "non-crystalline" or "amorphous" may mean an arbitrary solid material that lacks a lattice structure (for example, three-dimensional order) and may be understood as opposite to the term "crystalline" or "crystalloid".

The "dehydrogenation" may mean a reaction by which hydrogen in a compound is removed.

The "impregnation" may refer to a method of preparing a catalyst through drying and calcination after a support such as alumina, silica, or titania having a large surface area is impregnated with a solution in which a catalyst precursor is dissolved. Among the impregnations, incipient wetness impregnation is the most widely used method and may mean a method of preparing a catalyst by supporting an impregnation solution on the catalyst support in an amount corresponding to the pore volume of the catalyst support.

The "sol-gel method" may mean a method involving dissolving a catalyst precursor in an organic solvent or aqueous medium having a relatively high boiling point, then adding a support ingredient to the solution, and then gradually performing hydrolysis.

The "one-pot synthesis" may mean a synthesis method of obtaining a target compound by a method in which the process of adding the reactant of the next step in a single reaction vessel and conducting the reaction is continuously performed without separately purifying the product (intermediate product) of individual step during synthesis when a target compound is synthesized by a reaction process including two or more steps.

A "composite oxide" may mean an oxide in which two or more oxides are composited.

The "peptization" may mean formation of a stable colloidal solution and specifically may mean a process in which the flocculated or coagulated colloid returns to the initial dispersed state.

A "salt" may generically mean a compound in which a metal cation is bonded to an inorganic anion or organic anionic species.

A "complex" may mean a structure consisting of a central atom or ion and a molecule or anion (specifically, ligand) surrounding the central atom or ion while coordinating therewith.

Dehydrogenation Catalyst

According to an embodiment, a catalyst suitable for conversion of a hydrocarbon feedstock, in particular C4 hydrocarbons into butadiene through dehydrogenation is provided.

Figure 1:
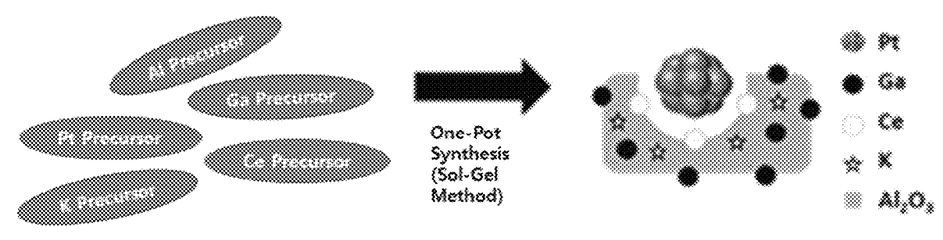
FIG. 1 is a diagram schematically illustrating distribution characteristics of ingredients in a composite oxide catalyst prepared from a first transition metal precursor, a second transition metal precursor, a hydrogen active metal precursor, a doping metal (for example, alkali metal and/or alkaline earth metal) precursor, and an alumina precursor through one-pot synthesis by a sol-gel method according to an embodiment.

FIG. 1 schematically illustrates the distribution characteristics of ingredients in a composite oxide catalyst prepared from (i) a gallium (Ga) precursor as a first transition metal precursor, (ii) a cerium (Ce) precursor as a second transition metal precursor, (iii) a platinum (Pt) precursor as a hydrogen active metal precursor, (iv) a potassium (K) precursor as a doping metal precursor, and an alumina precursor according to an exemplary embodiment.

Referring to the drawing, individual components constituting the catalyst may be distributed at a high degree of dispersion through one-pot synthesis by a sol-gel method. Specifically, the hydrogen active metal (for example, a noble metal such as platinum (Pt)) in the catalyst is at least partially (that is, partially or wholly) covered or surrounded by alumina into which the first transition metal (or the first transition metal and the second transition metal) and the doping metal are uniformly incorporated (for example, contained in a solid solution form). In this regard, when alumina ($Al_2O_3$) containing the first transition metal (or first and second transition metals) and the doping metal partially covers the hydrogen active metal particles, it may exist in a strap (or band) form. Alternatively, the catalyst may be in a form in which an alumina (namely, alumina containing the first transition metal and the doping metal) shell is formed on a hydrogen active metal core.

When the hydrogen active metal is covered or surrounded by alumina as illustrated, a sintering phenomenon caused by collision or coalescence between hydrogen active metal clusters may be effectively suppressed.

According to an exemplary embodiment, a second transition metal may be additionally introduced into the catalyst together with the first transition metal, and the second transition metal may chemically interact with the hydrogen active metal to suppress the sintering phenomenon and better disperse hydrogen active metal.

Furthermore, when the hydrogen active metal, the first transition metal (optionally, the second transition metal), and the doping metal (alkali metal or alkaline earth metal) are subjected to one-pot synthesis together with alumina by a sol-gel method, these active ingredients can effectively act by increasing the degree of dispersion of the first transition metal (or the first transition metal and the second transition metal) in alumina. In particular, a phenomenon in which the doping metal (alkali metal and/or alkaline earth metal) mixed together therewith blocks the active sites present on the outer surface of the catalyst may be minimized, and at the same time, the acid sites present in alumina may be suppressed.

According to an embodiment, the first transition metal may be at least one selected from the group consisting of gallium, vanadium, chromium, manganese, molybdenum, and zinc but is not necessarily limited thereto. In a particular embodiment, the first transition metal may be gallium, and this is because gallium may effectively form a solid solution with alumina and exhibit high selectivity for double bonds in the dehydrogenation. When the content of the first transition metal in the dehydrogenation catalyst is too low, the number of active sites decreases and the desired level of catalytic activity may not be achieved. When the content of the first transition metal is too high, it may be difficult to effectively use the transition metal active sites. In consideration of the above, in an example, the content of the first transition metal may be determined in a range of, for example, about 0.1% to 20% by weight, specifically about 0.5% to 10% by weight, more specifically about 1% to 5% by weight based on the weight of alumina in the final catalyst, but this may be understood as illustrative purposes.

According to an embodiment, the hydrogen active metal in the catalyst may be at least one selected from the group consisting of elements belonging to groups 8, 9, 10, and 11 of the periodic table. According to an exemplary embodiment, the hydrogen active metal may be at least one selected from the group consisting of Co, Ni, Cu, Ru, Rh, Pd, Ag, Ir, Pt, and Au. According to a particular embodiment, the hydrogen active metal may be at least one selected from the group consisting of Pt, Pd, and Ni and may in particular be a noble metal such as Pt. At this time, platinum (Pt) may be advantageous since platinum not only has excellent hydrogenation/dehydrogenation activity but also has a characteristic of exhibiting relatively suppressed sintering as compared to other hydrogen active metals.

As described above, unlike the dehydrogenation of propane, side reactions such as cracking and hydroisomerization may easily occur in the course of converting C4 hydrocarbons (for example, butane, butene, or a mixture of butane and butene) having single bonds or one double bond into butadiene (for example, 1,3-butadiene) containing two double bonds through dehydrogenation. In particular, the generation of C1 hydrocarbons and/or C2 hydrocarbons by hydrogenolysis also tends to be promoted than in the dehydrogenation of propane. In consideration of this, in an embodiment, it should be noted that the content of the hydrogen active metal in the catalyst is decreased to a significantly low level as compared to the conventionally acceptable level along with the incorporation of doping metal in the course of one-pot synthesis reaction by the sol-gel method.

According to an exemplary embodiment, the content of the hydrogen active metal may be determined in a range of, for example, about 0.1% by weight or less, specifically about 0.03% to 0.09% by weight, more specifically about 0.05% to 0.08% by weight based on the weight of alumina in the final catalyst.

The excessive acid sites of alumina are properly controlled by introducing a certain doping metal (e.g., alkali metal and/or alkaline earth metal) in the course of one-pot synthesis by the sol-gel method while decreasing the content of the hydrogen active metal, and as a result, the conversion of the feedstock may be slightly lowered but the selectivity and yield of butadiene may be improved as a whole as side reactions during the dehydrogenation are suppressed as much as possible. However, when the content of the hydrogen active metal is too low, the yield of butadiene may decrease by insufficient interaction with the first transition metal, so it may be advantageous to properly control the content of the hydrogen active metal in the above content range taking into consideration the influence of other factors (for example, the kind of hydrogen active metal, the content of the doping metal, and the like). Further, the particle size of the hydrogen active metal may be in a range of, for example, about 0.5 to 10 nm, specifically about 0.6 to 3 nm, more specifically about 0.8 to 1.5 nm.

According to an exemplary embodiment, the second transition metal is an ingredient optionally introduced into the catalyst in order to suppress agglomeration or sintering of the hydrogen active metal, and at least one may be selected from the group consisting of zirconium (Zr) and lanthanide metals, for example. According to a specific embodiment, the second transition metal may be cerium (Ce) and/or zirconium (Zr), and in another embodiment, the second transition metal may be cerium (Ce).

The second transition metal may be introduced together with other metal precursors and the alumina precursor in the course of one-pot synthesis by the sol-gel method, and as a result, the second transition metal may exist in a form of being uniformly contained in the alumina support (that is, can form a solid solution) similar to the first transition metal and, in particular embodiment, may exist in a monoatomic form. In this regard, the content of the second transition metal may be determined in a range of, for example, about 0.1% to 20% by weight, specifically about 0.5% to 10% by weight, more specifically about 1% to 5% by weight based on the weight of alumina in the final catalyst, but the content range may be changed depending on the kind of metal.

According to an embodiment, the dehydrogenation catalyst further contains at least one doping metal selected from the group consisting of elements belonging to groups 1 and 2 of the periodic table, particularly, alkali metals and alkaline earth metals. Such a doping metal may be more evenly distributed in the acid sites of alumina by being introduced during the one-pot synthesis reaction by the sol-gel method, and a decrease in activity due to blocking of the metal surface may be suppressed. In an exemplary embodiment, the doping metal may be at least one selected from the group consisting of K, Cs, Mg, and Ca. According to a specific embodiment, the doping metal may be potassium (K), and this is because potassium not only provides a function of suppressing the acid sites but also may be advantageous for commercialization since its precursor price is low. However, the kinds of doping metals listed above may be understood as illustrative purposes.

As described above, in the case of a catalyst synthesized by adding a doping metal in a one-pot manner by a sol-gel method, the content of the doping metal may be determined in a range of, for example, about 0.01% to 5% by weight, specifically about 0.05% to 2% by weight, more specifically about 0.3% to 1% by weight based on the weight of alumina in the final catalyst. In this regard, when the content of the doping metal is too high, the doping metal may rather block the active sites of the catalyst and deteriorates the catalytic activity. When the content of the doping metal is too low, the acid sites in the catalyst may not be sufficiently suppressed and the improvement in butadiene selectivity is limited. Hence, it may be advantageous to properly control the content of the doping metal in the above range. However, the above content range may be changed depending on the kind of doping metal, the kinds of other active metals, and the like.

According to an exemplary embodiment, the ratio between metals may be more properly controlled even in the content ranges of the respective metal components. By way of example, the molar ratio of the first transition metal/ hydrogen active metal may be controlled in a range of, for example, about 3 to 3000, specifically about 15 to 900, more specifically about 35 to 280. Further, the molar ratio of the first transition metal/doping metal may be controlled in a range of, for example, about 0.01 to 1000, specifically about 0.15 to 100, more specifically about 0.5 to 10. In addition, when the catalyst further contains a second transition metal, the molar ratio of the first transition metal/second transition metal may be controlled in a range of, for example, about 0.01 to 400, specifically about 0.1 to 40, more specifically about 0.4 to 10. These ranges of ratios between metals may be understood as illustrative purposes.

As alumina in the dehydrogenation catalyst surrounds or covers the hydrogen active metal in a state of containing (or supporting) the first transition metal (or first and second transition metals) and the doping metal, it may provide a function of physically suppressing sintering of the hydrogen active metal. According to a specific embodiment, alumina may have gamma crystallinity.

As described above, by controlling the acid sites of the alumina support in the catalyst through the incorporation of the doping metal and, at the same time, controlling the content of the hydrogen active metal to be lower than that of the conventionally acceptable level, the conversion of C4 hydrocarbons (specifically, C4 hydrocarbons having single bonds or one double bond) into butadiene at the time of dehydrogenation may be efficiently enhanced. In this aspect, the amount of acid sites in the dehydrogenation catalyst may be in a range of, for example, about 50 to 700 μmol/g, specifically about 100 to 500 μmol/g, more specifically about 200 to 400 μmol/g, particularly specifically about 250 to 300 μmol/g when being measured by ammonia ($NH_3$) temperature programmed desorption (TPD), but this may be understood as illustrative purposes.

According to an exemplary embodiment, the specific surface area (BET) of the catalyst may be in a range of, for example, at least about 10 to 400 $m^2/g$, specifically about 100 to 350 $m^2/g$, more specifically about 150 to 300 $m^2/g$. The pore volume in the catalyst may be in a range of, for example, about 0.1 to 1 $cm^3/g$, specifically about 0.15 to 0.7 $cm^3/g$, more specifically about 0.2 to 0.5 $cm^3/g$. The pore size (average diameter) may be in a range of, for example, about 1 to 50 nm, specifically about 2 to 30 nm, more specifically about 3 to 10 nm. It is to be understood that the above numerical ranges have been described as illustrative purposes.

Process for preparing dehydrogenation catalyst According to an embodiment, there is provided a process for preparing a catalyst in the form of a composite oxide capable of converting a feedstock containing C4 hydrocarbons into butadiene (specifically, 1,3-butadiene), and one-pot synthesis by a sol-gel method may be applied for this.

In this regard, the sol-gel method may comprise converting a sol into a gel through hydrolysis and polymerization/ condensation of compounds in a solution of organic or inorganic compounds of metals and heating the converted gel to form an oxide. This sol-gel method may be broadly divided into two depending on the gelation aspect.

As a first method, a sol that is a raw material solution is formed by dispersing colloid particles in a solution, and then gelled by destabilization of the sol state (colloidal method).

As a second method, a sol is prepared using a metal-organic compound such as an alkoxide as a starting material, and this may be converted into a gel state through hydrolysis and polymerization/condensation. The second method is suitable for formation of a uniform multicomponent system.

In this regard, in the present embodiment, any methods known in the art may be applied as the sol-gel route as described above.

In an embodiment, the step of preparing a precursor solution by dissolving a precursor of each of the first transition metal (or first and second transition metal), hydrogen active metal, doping metal (specifically, alkali metal and/or alkaline earth metal), and alumina in a solvent may be performed. At this time, the solvent may be an aqueous medium (specifically water, more specifically distilled water), and the amount of each of the precursors of the individual metals and precursor of alumina added to the solvent may be determined in consideration of the ratio between components in the final catalyst. According to an exemplary embodiment, the amount of the solvent in the precursor solution may be controlled so that the concentration of the total precursors is in a range of, for example, about 0.005 to 2 M, specifically about 0.01 to 0.1 M, more specifically about 0.015 to 0.02 M, but this may be understood as illustrative purposes.

According to an exemplary embodiment, the aqueous precursor solution may be prepared by two steps. Specifically, a metal precursor solution may be first prepared by dissolving metal precursors, namely, a first transition metal precursor (or first and second transition metal precursors), a hydrogen active metal precursor, and a doping metal precursor in a liquid medium (aqueous medium). Thereafter, the alumina precursor may be added to the metal precursor solution to hydrolyze the alumina precursor. At this time, the hydrolysis may be performed at a temperature of, for example, about 323 to 423 K, specifically about 343 to 393 K, more specifically about 353 to 373 K, and hydrolysis may be performed under stirring conditions if necessary.

According to an exemplary embodiment, the alumina precursor may be an $Al^{3+}$ precursor, for example, an organic or inorganic acid salt, an alkoxide, or a complex of aluminum or a combination thereof. Such an alumina precursor may be, for example, at least one selected from the group consisting of aluminum acetate, aluminum acetylacetonate, aluminum t-butoxide, aluminum sec-butoxide, aluminum pentoxide, aluminum ethoxide, aluminum isopropoxide, aluminum tributoxide, aluminum fluoride, aluminum chloride, aluminum bromide, aluminum iodide, aluminum sulfate, aluminum nitrate, and any hydrate thereof, but this may be understood as illustrative purposes. According to a specific embodiment, the alumina precursor may be aluminum nitrate and/or a hydrate thereof (aluminum nitrate nonahydrate). Exemplarily, the alumina precursor may be added to the metal precursor solution as the precursor itself or in a solution (specifically, an aqueous solution) form (for example, a concentration of about 0.1 to 1.5 M). At this time, the amount of the alumina precursor added may be selected in consideration of the content of alumina in the final catalyst as described above.

As the precursors of metal components, various salts, complexes, and the like of the corresponding metals known in the art may be used without limitation as long as they may be subjected to sol-gel synthesis together with the alumina precursor.

According to an exemplary embodiment, as the precursor of the first transition metal (or each of the first transition metal and the second transition metal), at least one may be selected from a nitrate, a sulfate, an acetate, a formate, or a halide (for example, a chloride, an iodide, or the like) of the corresponding metal. At this time, when the first transition metal and the second transition metal are both used, the precursors of these two may be the same salt or complex or different salts or complexes.

According to an exemplary embodiment, the precursor of the hydrogen active metal may also be used in the form of various salts (organic or inorganic salts), complexes, and the like. In this regard, when the hydrogen active metal is platinum, hydrides, fluorides (for example, $PtF_6$, $PtF_4$, $[PtF_5]_4$, and the like), chlorides (for example, $PtCl_3$, $PtCl_4$, $Pt_6Cl_{12}$, and the like), bromides ($PtBr_3$, $PtBr_4$, and the like), iodides (for example, $PtI_2$, $PtI_3$, $PtI_4$, and the like), oxides (for example, PtO, $PtO_2$, PtO, and the like), sulfides (for example, PtS, $PtS_2$, and the like), carbonyls (for example, $Pt(CO)_4$), and/or complexes (for example, $[PtCl_2(NH_3)_2]$, $[PtCl_2(NH_3)_2]$, $K_2[PtCl_6]$, $K_2[Pt(CN)_4]$, $PtCl_4 \cdot 5H_2O$, $K[PtCl_3(NH_3)]$, $Na_2[PtBr_6] \cdot 6H_2O$, $(NH_4)_2[PtBr_6]$, $K_2[PtI_6]$, $(NH_4)_2[PtCl_6]$, $K_2[Pt(CN)_6]$, $(NH_4)_2[PtCl_4]$, $K_2[Pt(NO_2)_4]$, $K[PtCl_3(C_2H_4)] \cdot H_2O$ $[Pt(NH_3)_4](NO_3)_2$, $H_2PtCl_6$, and the like) may be used, but the precursor of the hydrogen active metal is not limited thereto. The substances listed above may be used alone or in combination.

According to an exemplary embodiment, the precursor of the doping metal, specifically, an alkali metal and/or an alkaline earth metal, may be various organic salts or inorganic salts and may be, for example, at least one selected from a hydroxide, a nitrate, a chloride, a carbonate, or a sulfate. Examples of such a doping metal precursor may be at least one selected from sodium nitrate, sodium sulfate, sodium chloride, magnesium sulfate, potassium nitrate, potassium sulfate, potassium chloride, sodium ascorbate or the like.

According to an exemplary embodiment, during or after the hydrolysis, a step of peptizing alumina may be performed under the addition of an acid. At this time, the added acid is not particularly limited as long as it is capable of promoting the hydrolysis of aluminum precursor by increasing the number of protons ($H^+$) in the solution and may be, for example, at least one selected from the group consisting of nitric acid, hydrochloric acid, and sulfuric acid. The amount of acid added may be controlled so that the pH of the precursor solution is in a range of, for example, about 1 to 5, specifically about 2 to 4, more specifically about 2 to 3. In this regard, the molar ratio of acid/Al may be controlled in a range of, for example, about 0.05 to 1, specifically about 0.1 to 0.6, more specifically about 0.2 to 0.4.

When the reaction product is formed in this manner, a drying step may be performed to remove the solvent (specifically, moisture) from the liquid medium containing the product. In this drying step, a drying method known in the art, for example, a thermal drying method may be applied depending on the moisture drying conditions. Exemplarily, the drying temperature may be controlled in a range of, for example, about 50° C. to 200° C., specifically about 70° C. to 120° C., more specifically about 80° C. to 100° C., and the drying time may be controlled in a range of, for example, about 3 to 24 hours, specifically about 6 to 15 hours, more specifically about 8 to 14 hours, but this may be understood as illustrative purposes. The drying step may be performed under stirring, and it may be advantageous to completely remove the solvent component. In some cases, a step of removing the precursors which have not participated in the reaction using water, specifically distilled water, and drying the residue may be performed at least one time.

The dried product may be subjected to a heat treatment, namely, calcination to prepare a catalyst in a composite oxide form, specifically, a metal-alumina form. In an exemplary embodiment, the heat treatment may be performed under a temperature condition of, for example, about 350° C. to 1000° C., specifically about 400° C. to 900° C., more specifically about 500° C. to 800° C. In this regard, when the heat treatment temperature is too low or the heat treatment time is less than a certain level, the formation of metal-alumina composite oxide may not be sufficient. When the heat treatment temperature is too high or the heat treatment time exceeds a certain level, the metal-alumina phase may be denatured. Hence, it may be advantageous to control the heat treatment in the condition ranges as described above, but the heat treatment conditions are not necessarily limited thereto.

At this time, the heating rate may be controlled in a range of, for example, about 1° C./min to 10° C./min, specifically about 1.5° C./min to 5° C./min, more specifically about 2° C./min to 4° C./min. Exemplarily, the heat treatment time may be controlled in a range of, for example, about 1 to 12 hours, specifically about 2 to 10 hours, more specifically about 3 to 5 hours. The heat treatment may be performed in an oxygen-containing atmosphere (namely, conditions of supplying oxygen molecules), an air (specifically dry air) atmosphere, or a mixed gas atmosphere of oxygen and an inert gas (for example, nitrogen, neon, argon or the like).

As described above, by mixing all catalyst components together by a sol-gel method and preparing a catalyst in a one-pot manner, a dehydrogenation catalyst may be prepared by only one time of drying and heat treatment.

Dehydrogenation

According to another embodiment of the present disclosure, paraffins, specifically light paraffins (more specifically, light paraffins having 2 to 5 carbon atoms) may be converted into olefins or diolefins by dehydrogenation using the catalyst in a composite oxide form described above. Examples of such dehydrogenation include converting methane into an olefin, converting propane into propylene, converting butane into butene or butadiene, and converting cyclohexane into benzene.

In this regard, it should be noted that the catalyst according to the present embodiment may be advantageously applied to prepare products containing butadiene, specifically 1,3-butadiene in an increased content by direct dehydrogenation of a feedstock containing C4 hydrocarbons having single bonds or one double bond. At this time, the "direct dehydrogenation" may be dehydrogenation that does not require the addition of oxygen, specifically non-oxidative dehydrogenation.

According to an exemplary embodiment, the feedstock may comprise C4 hydrocarbons (specifically, n-butane, isobutane, 1-butene, 2-butene, isobutene, or mixtures thereof). Optionally, the feedstock may further contain hydrocarbons other than C4 hydrocarbons. Examples of the additionally containable hydrocarbons include at least one selected from methane, ethane, ethylene, propane, and propylene.

According to an exemplary embodiment, the content of C4 hydrocarbons in the feedstock may be in a range of, for example, at least about 10 mol %, specifically at least about 50 mol %, more specifically at least about 90 mol %.

In a specific embodiment, the amount of hydrocarbons having less than 4 carbon atoms may be, for example, less than about 90 mol %, specifically less than about 50 mol %, more specifically less than about 10 mol %. In another specific embodiment, the amount of hydrocarbons having more than 4 carbon atoms may be, for example, less than about 90 mol %, specifically less than about 50 mol %, more specifically less than about 10 mol %.

According to a specific embodiment, the amount of C4 paraffins among the C4 hydrocarbons may be, for example, at least about 10 mol %, specifically at least about 50 mol %, more specifically at least about 90 mol %, and C4 paraffins may be contained up to 100 mol %. In an exemplary embodiment, the feedstock may be a fraction derived from BBR-1 or BBR-3 during the refining process.

According to an embodiment, the dehydrogenation may be performed by bringing the feedstock into contact with the catalyst under dehydrogenation conditions. At this time, the reaction system may be a continuous reaction system (specifically, a fixed bed reactor, a moving bed reactor, a fluidized bed reactor or the like) or a batch reaction system. According to a specific embodiment, a fixed bed reactor may be used. According to an exemplary embodiment, the feedstock may be heated (for example, about 100° C. to 700° C.) before being introduced into the dehydrogenation zone. The feedstock may be brought into contact with the catalyst in an upward flow, downward flow, or the like manner. The feedstock also may exist as a liquid phase, a gaseous-liquid mixed phase, or a gaseous phase in the reaction zone, and in a specific embodiment, the feedstock may be a gaseous phase.

According to an exemplary embodiment, prior to the dehydrogenation, the catalyst may be pretreated in an inert atmosphere under temperature increasing conditions. At this time, the inert atmosphere may be implemented by flowing an inert gas. The inert gas may be at least one selected from nitrogen, neon, argon, helium, or the like, and the pretreatment temperature may be determined in a range of, for example, about 300° C. to 800° C., specifically about 400° C. to 750° C., more specifically about 500° C. to 700° C.

According to an exemplary embodiment, the dehydrogenation (specifically, direct dehydrogenation) temperature may be set in a range of, for example, about 300° C. to 800° C., specifically about 400° C. to 700° C., more specifically about 500° C. to 650° C. In a specific embodiment, in the process of preparing butadiene from a feedstock containing C4 hydrocarbons such as butane and/or butene, the reaction temperature may be set to approximately 600° C. When the dehydrogenation temperature is too low, the reactant may not be activated to a degree sufficient for the reaction, and the thermodynamic equilibrium conversion may be lowered. When the reaction temperature is too high, the decomposition of the reactant, in particular C4 hydrocarbons, may mainly occur. Hence, it may be advantageous to properly control the reaction temperature in the aforementioned range in consideration of this. However, these reaction temperature conditions may be understood as illustrative purposes, and may be changed depending on other reaction conditions (for example, composition of feedstock, reaction pressure, space velocity and the like).

According to an exemplary embodiment, in the case of a continuous reaction, it may be advantageous to control the space velocity so as to optimize the production amount of the desired product olefin, in particular butadiene while suppressing coking deposition due to side reactions. In this aspect, the weight hourly space velocity (WHSV) may be controlled in a range of, for example, about 0.5 to 100 $hr^{-1}$, specifically about 1 to 50 $hr^{-1}$, more specifically about 2 to 25 $hr^{-1}$.

According to an exemplary embodiment, at the time of dehydrogenation, the feedstock may be introduced into the reaction zone together with a diluent gas. In this case, the diluent gas is an inert gas or hydrogen, or steam, and the partial pressure thereof may be in a range of, for example, about 0 to 95 kPa, specifically about 50 to 90 kPa, more specifically about 60 to 85 kPa. The partial pressure of the feedstock (in particular C4 hydrocarbons) may be in a range of, for example, about 5 to 100 kPa, specifically about 10 to 50 kPa, more specifically about 15 to 30 kPa. The above-described dehydrogenation conditions may be changed depending on the composition of the feedstock, the contents and ratios of the active metals and the doping metals in the catalyst, and the like.

A product containing butadiene in an increased content may be formed by the above-described dehydrogenation, specifically by dehydrogenating C4 hydrocarbons having single bonds or one double bond in the feedstock. At this time, the hydrogen active metal is contained in the catalyst in a smaller amount as compared to a usual case, and the conversion of the reactant C4 hydrocarbons may be slightly decreased by the control of acid sites of alumina in association with the incorporation of doping metal, but side reactions (cracking/isomerization) are rather suppressed, and as a result, the selectivity and yield of butadiene, in particular 1,3-butadiene, that is the desired product, may be improved to a significant level as a whole. In this regard, according to an exemplary embodiment, the conversion and the butadiene selectivity may be levels of, for example, at least about 60% (specifically at least about 65%, more specifically about 70% to 85%) and at least about 15% (specifically at least about 18%, more specifically about 20% to 25%), respectively. However, this may be understood as illustrative purposes.

In order to recover butadiene from the product having an increased butadiene content, any separation and recovery processes known in the art may be performed and, for example, an extractive distillation may be used.

The present invention may be more clearly understood by the following Examples, and the following Examples are for illustrative purposes only and are not intended to limit the scope of the invention.

EXAMPLES

The precursor compounds used in the present Examples are as follows.

Tetraamineplatinum nitrate ($Pt(NH_3)_4(NO_3)_2$) was obtained from Sigma-Aldrich.

Gallium nitrate $Ga(NO_3)_3$ was obtained from Sigma-Aldrich.

Cerium nitrate was obtained from Sigma-Aldrich.

Potassium nitrate ($KNO_3$) was obtained from Sigma-Aldrich.

Aluminum isopropoxide ($C_9H_{21}AlO_3$) was obtained from Sigma-Aldrich.

Preparation Example 1

Preparation of First Transition Metal-Noble Metal-Second Transition Metal-Doping Metal-Alumina Composite Catalyst (0.1Pt-3Ga-1Ce-0.5K/$Al_2O_3$) Through One-Pot Synthesis by Sol-Gel Method 0.04 g of tetraamineplatinum nitrate, 2.27 g of gallium nitrate, 0.62 g of cerium nitrate, and 0.26 g of potassium nitrate were weighed, respectively, so that the contents of platinum, gallium, cerium, and potassium were about 0.1% by weight, about 3% by weight, about 1% by weight, and about 0.5% by weight, respectively, based on the weight of alumina in the final catalyst, and added to about 700 ml of distilled water to prepare an aqueous solution, and this aqueous solution was stirred while maintaining the temperature at about 358 K.

80.1 g of aluminum isopropoxide was added to the aqueous solution in which the respective metal precursors were completely dissolved, and the mixture was further stirred at about 358 K for about 30 minutes. Thereafter, 8.1 g of nitric acid ($HNO_3$, about 61% solution) was added to the solution, in which aluminum isopropoxide was hydrolyzed, to perform peptization, and the solution in which the synthesis reaction had been completed was continuously stirred for 12 hours until the entire distilled water evaporated.

The dried product was taken out and calcined in the dry air at about 1023 K for about 2 hours, and as a result, a catalyst was obtained. Hereinafter, the obtained catalyst is denoted as "0.1Pt-3Ga-1Ce-0.5K/$Al_2O_3$ (solgel)".

Preparation Example 2

Preparation of First Transition Metal-Noble Metal-Second Transition Metal-Doping Metal-Alumina Composite Catalyst (0.08Pt-3Ga-1Ce-0.5K/$Al_2O_3$ and 0.05Pt-3Ga-1Ce-0.5K/$Al_2O_3$) with Decreased Platinum Content Through One-Pot Synthesis by Sol-Gel Method A catalyst was prepared so that gallium, cerium, and potassium were about 3% by weight, about 1% by weight, and about 0.5% by weight, respectively, based on the weight of alumina in the final catalyst, and platinum was about 0.08% by weight or 0.05% by weight based on the weight of alumina in the final catalyst.

For the two catalysts, 2.27 g of gallium nitrate, 0.62 g of cerium nitrate, and 0.26 g of potassium nitrate are weighed, respectively, and added to about 700 ml of distilled water to prepare an aqueous solution. In addition, when the platinum content in the final catalyst was 0.08% by weight and 0.05% by weight, respectively, 0.032 g of tetraamineplatinum nitrate and 0.02 g of tetraamineplatinum nitrate were added to the aqueous solution, respectively.

Subsequently, the two catalysts were prepared according to the same procedure as in Preparation Example 1. The two catalysts were denoted as "0.08Pt-3Ga-1Ce-0.5K/$Al_2O_3$ (solgel)" and "0.05Pt-3Ga-1Ce-0.5K/$Al_2O_3$ (solgel)," respectively depending on the content of platinum in the catalyst.

Comparative Preparation Example 1

Preparation of First Transition Metal-Noble Metal-Alumina Composite Catalyst (0.1Pt-3Ga/$Al_2O_3$) Through One-Pot Synthesis by Sol-Gel Method 2.27 g of gallium nitrate and 0.04 g of tetraamineplatinum nitrate were weighed, respectively, so that the contents of gallium and platinum were about 3% by weight and 0.1% by weight, respectively, based on the weight of alumina in the final catalyst, and added to about 700 ml of distilled water to prepare an aqueous solution, and this aqueous solution was stirred while maintaining the temperature at about 358 K.

80.1 g of aluminum isopropoxide was added to the aqueous solution in which the respective metal precursors were completely dissolved, and the mixture was further stirred at about 358 K for about 30 minutes. Thereafter, 8.1 g of nitric acid ($HNO_3$, about 61% solution) was added to the solution, in which aluminum isopropoxide was hydrolyzed, to perform peptization, and the solution in which the synthesis reaction had been completed was continuously stirred for 12 hours until the entire distilled water evaporated.

The dried product was taken out and calcined in the dry air at about 1023 K for about 2 hours, and as a result, a catalyst was obtained. Hereinafter, the obtained catalyst is denoted as "0.1Pt-3Ga/Al$_2$O$_3$ (solgel)".

Comparative Preparation Example 2

Preparation of First Transition Metal-Noble Metal-Second Transition Metal-Alumina Composite Catalyst (0.1Pt-3Ga-1Ce/Al$_2$O$_3$ (Solgel)) Through One-Pot Synthesis by Sol-Gel Method and First Transition Metal-Noble Metal-Second Transition Metal-Doping Metal-Alumina Composite Catalyst (0.1Pt-3Ga-1Ce-0.5K(imp)/Al$_2$O$_3$ (Solgel)) in which Potassium is Introduced by Impregnation Method 0.04 g of tetraamineplatinum nitrate, 2.27 g of gallium nitrate, and 0.62 g of cerium nitrate were weighed, respectively, so that the contents of platinum, gallium, and cerium were about 0.1% by weight, about 3% by weight, and about 1% by weight, respectively, based on the weight of alumina in the final catalyst, and added to about 700 ml of distilled water to prepare an aqueous solution, and this aqueous solution was stirred while maintaining the temperature at about 358 K.

80.1 g of aluminum isopropoxide was added to the aqueous solution in which the respective metal precursors were completely dissolved, and the mixture was further stirred at about 358 K for about 30 minutes. Thereafter, 8.1 g of nitric acid (HNO$_3$, about 61% solution) was added to the solution, in which aluminum isopropoxide was hydrolyzed, to perform peptization, and the solution in which the synthesis reaction had been completed was continuously stirred for 12 hours until the entire distilled water evaporated.

The dried product was taken out and calcined in the dry air at about 1023 K for about 2 hours, and as a result, a catalyst was obtained. Hereinafter, the obtained catalyst is denoted as "0.1Pt-3Ga-1Ce/Al$_2$O$_3$ (solgel)".

In addition, potassium nitrate was added to the catalyst (0.1Pt-3Ga-1Ce/Al$_2$O$_3$ (solgel)) synthesized as above by incipient wetness impregnation so that the potassium content was about 0.5% by weight based on the weight of alumina in the final catalyst, then calcination was performed under the same conditions to obtain a catalyst. Hereinafter, the obtained catalyst is denoted as "0.1Pt-3Ga-1Ce-0.5K(imp)/Al$_2$O$_3$ (solgel)".

Example 1

Measurement of n-Butane Dehydrogenation Reactivity

Each of the catalyst samples, namely 0.1Pt-3Ga/Al$_2$O$_3$ (solgel), 0.1Pt-3Ga-1Ce/Al$_2$O$_3$ (solgel), 0.1Pt-3Ga-1Ce-0.5K/Al$_2$O$_3$ (solgel), 0.08Pt-3Ga-1Ce-0.5K/Al$_2$O$_3$ (solgel), 0.05Pt-3Ga-1Ce-0.5K/Al$_2$O$_3$ (solgel), and 0.1Pt-3Ga-1Ce-0.5K(imp)/Al$_2$O$_3$ (solgel) prepared in Preparation Examples and Comparative Preparation Examples was subjected to an n-butane dehydrogenation experiment.

The dehydrogenation was conducted in a fixed-bed continuous flow reactor using about 0.3 g of catalyst, and all samples were treated in-situ at about 873 K and a N$_2$ flow rate of about 200 sccm prior to the reaction. The dehydrogenation of n-butane was conducted (WHSV: about 2.4 hr$^{-1}$, temperature: 873 K, P$_{N2}$: about 83 kPa, and P$_{butane}$: about 17 kPa).

The n-butane conversion and butadiene selectivity/yield after 10 minutes from the start of injection of reactants were analyzed using on-line GC, and the results are presented in the following Table 1.

TABLE 1

| Catalyst | WHSV (hr$^{-1}$) | n-C4 Conversion | C1-C3 (selectivity/yield) | Isomerization (selectivity/yield) | Butadiene (selectivity/yield) |
|---|---|---|---|---|---|
| 0.1Pt—3Ga—1Ce/Al$_2$O$_3$ (solgel) | 2.4 | 80.3 | 14.5/11.6 | 3.5/2.8 | 20.8/16.7 |
| 0.1Pt—3Ga—1Ce—0.5K/Al$_2$O$_3$ (solgel) | 2.4 | 73.5 | 15.7/11.5 | 1.8/1.3 | 22.8/16.8 |
| 0.08Pt—3Ga—1Ce—0.5K/Al$_2$O$_3$ (solgel) | 2.4 | 76.4 | 14.0/10.7 | 1.7/1.3 | 23.6/18.0 |
| 0.05Pt—3Ga—1Ce—0.5K/Al$_2$O$_3$ (solgel) | 2.4 | 72.9 | 13.8/10.1 | 1.5/1.1 | 23.7/17.3 |
| 0.1Pt—3Ga/Al$_2$O$_3$ (solgel) | 2.4 | 80.9 | 15.8/12.8 | 4.3/3.5 | 20.3/16.4 |
| 0.1Pt-3Ga—1Ce—0.5K(imp)/Al$_2$O$_3$ (solgel) | 2.4 | 70.5 | 13.9/9.8 | 1.8/1.3 | 23.0/16.2 |

According to the above table, it has been confirmed that the highest butadiene yield is obtained when 0.08Pt-3Ga-1Ce-0.5K/Al$_2$O$_3$ (solgel) catalyst in which a one-pot synthesis reaction by a sol-gel method was conducted using precursors of platinum, gallium, cerium, and potassium and the platinum content in the catalyst was controlled to about 0.08% by weight based on the weight of alumina was used.

Considering the results presented in the above table, it can be seen that the platinum content is preferably about 0.1% by weight or less based on the weight of alumina in the catalyst since gallium serves as the main active sites. In particular, since the hydrogenolysis and/or isomerization at the time of dehydrogenation of n-butane is promoted as compared to the case of propane dehydrogenation, the most favorable butadiene yield may be obtained when the platinum content is lowered to about 0.08% by weight. In the case of post-supporting potassium by incipient wetness impregnation in order to suppress acid sites in the alumina support as in 0.1Pt-3Ga-1Ce-0.5K(imp)/Al$_2$O$_3$ (solgel) catalyst, it can be seen that potassium rather blocks the surface of active metal to decrease the n-butane conversion and, as a result, the overall butadiene yield is decreased.

Example 2

Measurement of Dehydrogenation Reactivity Using Mixed Feedstock with n-Butane:Butene Ratio of 6:4

The catalysts, namely 0.1Pt-3Ga-1Ce-0.5K/Al$_2$O$_3$ (solgel), 0.08Pt-3Ga-1Ce-0.5K/Al$_2$O$_3$ (solgel), and 0.05Pt-3Ga-1Ce-0.5K/Al$_2$O$_3$ (solgel) prepared by varying the platinum content in Preparation Examples 1 and 2 were subjected to a dehydrogenation experiment using a mixed feedstock having a n-butane:butene ratio of 6:4.

The dehydrogenation was conducted in a fixed-bed continuous flow reactor using about 0.3 g of catalyst, and all samples were treated in-situ at about 873 K and a $N_2$ flow rate of about 200 sccm prior to the reaction.

The dehydrogenation of n-butane was conducted (WHSV: about 2.4 $hr^{-1}$, temperature: 873 K, $P_{N2}$: about 83 kPa, and $P_{mixfeed}$: about 17 kPa).

The n-butane conversion and butadiene selectivity/yield after 10 minutes from the start of injection of reactants were analyzed using on-line GC, and the results are presented in the following Table 2.

TABLE 2

| Catalyst | WHSV ($h^{-1}$) | n-Butane + butene conversion | C1-C3 yield (%) | Isomerization yield (%) | Butadiene yield (%) |
|---|---|---|---|---|---|
| 0.1Pt—3Ga—1Ce—0.5K/$Al_2O_3$ (solgel) | 2.4 | 28.8 | 10.6 | 3.1 | 15.2 |
| 0.08Pt—3Ga—1Ce—0.5K/$Al_2O_3$ (solgel) | 2.4 | 30.7 | 8.3 | 1.2 | 21.3 |
| 0.05Pt—3Ga—1Ce—0.5K/$Al_2O_3$ (solgel) | 2.4 | 28.5 | 7.9 | 1.1 | 19.5 |

According to the above table, in the experiment using a feedstock containing butene together with n-butane as well, it has been confirmed that the most favorable butadiene yield may be obtained when the platinum content is controlled to 0.08% by weight based on the weight of alumina in the catalyst.

Example 3

The catalysts, namely 0.1Pt-3Ga-1Ce/$Al_2O_3$ (solgel), 0.1Pt-3Ga-1Ce-0.5K/$Al_2O_3$ (solgel), and 0.1Pt-3Ga-1Ce-0.5K(imp)/$Al_2O_3$ (solgel) prepared by varying the presence or absence of potassium introduction and the potassium introduction step were subjected to an ammonia ($NH_3$) temperature programmed desorption (TPD) experiment.

$NH_3$ TPD was measured by Micromeritics AutoChem II equipment using about 0.5 g of catalyst, the sample was maintained at about 723 K and He 50 sccm for 2 hours, 15% $NH_3$/He gas was adsorbed to the sample at room temperature for 30 minutes, and the measurement was performed at room temperature to 723 K while flowing He 50 sccm. The amount of $NH_3$ desorbed at the desorption temperature is presented in the following Table 3.

TABLE 3

| Catalyst | $NH_3$ TPD (μmol/g) |
|---|---|
| 0.1Pt—3Ga—1Ce/$Al_2O_3$ (solgel) | 345 |
| 0.1Pt—3Ga—1Ce—0.5K/$Al_2O_3$ (solgel) | 283 |
| 0.1Pt—3Ga—1Ce—0.5K(imp)/$Al_2O_3$ (solgel) | 292 |

It has been confirmed that the amount of acid sites in the catalyst decreases as potassium is doped, and the amount of acid sites is measured to be the lowest in 0.1Pt-3Ga-1Ce-0.5K/$Al_2O_3$ (solgel) in which potassium has been introduced through one-pot synthesis by a sol-gel method.

The dehydrogenation catalyst for butadiene preparation according to an embodiment of the present disclosure can provide improved dehydrogenation activity by only one time of drying and heat treatment (calcination) since the dehydrogenation catalyst is produced from precursors of a plurality of metal components (transition metal, hydrogen active metal, and alkali or alkaline earth metal) and a precursor of alumina through one-pot synthesis by a sol-gel method. In particular, by adopting a method of introducing a precursor of a first transition metal as an active ingredient and a precursor of an alkali metal and/or an alkaline earth metal and a precursor of a hydrogen active metal (additionally a second transition metal) as auxiliary components into a precursor of alumina in the course of one-pot synthesis by the sol-gel method, the acid sites in the alumina support can be effectively controlled without deteriorating the activity of catalyst as compared to a usual impregnation method. At the same time, by decreasing the amount of hydrogen active metal (in particular noble metal such as platinum) used to a significantly low level as compared to the conventionally acceptable level, side reactions (isomerization, cracking, and the like) occurring in the course of conversion of C4 hydrocarbons into butadiene can be effectively suppressed. Furthermore, the advantages are provided that enhanced catalyst durability is exhibited in the course of dehydrogenation for converting C4 hydrocarbons into butadiene (in particular 1,3-butadiene) and the initial catalytic activity can be maintained as high as possible even when the dehydrogenation catalyst is regenerated and used.

While the present invention has been described with respect to the specific embodiments, it will be apparent to those skilled in the art that various changes and modifications may be made without departing from the spirit and scope of the invention as defined in the following claims.

What is claimed is:

1. A composite oxide catalyst for preparing 1,3-butadiene from C4 hydrocarbons via dehydrogenation, which comprises:
    at least one first transition metal selected from the group consisting of gallium, vanadium, chromium, manganese, molybdenum, and zinc;
    at least one hydrogen active metal selected from the group consisting of elements belonging to groups 8, 9, 10, and 11 of the periodic table;
    at least one doping metal selected from the group consisting of elements belonging to groups 1 and 2 of the periodic table; and
    alumina, wherein
    a content of the first transition metal is determined in a range of 0.1% to 20% by weight based on a weight of alumina,
    a content of the hydrogen active metal is determined at 0.09% by weight or less based on a weight of alumina,
    a content of the doping metal is determined in a range of 0.01% to 5% by weight based on a weight of alumina,
    the first transition metal and the doping metal are each contained in alumina in a solid solution form and the hydrogen active metal is surrounded by alumina containing the first transition metal and doping metal, whereby the doping metal is distributed in the acid sites of alumina to result in a controlled amount of acid sites, a molar ratio of the first transition metal/hydrogen active metal is controlled in a range of 35 to 3000, and a molar ratio of the first transition metal/doping metal is controlled in a range of 0.5 to 10.

2. The composite oxide catalyst according to claim 1, wherein the dehydrogenation catalyst further comprises at least one second transition metal selected from the group consisting of cerium and zirconium, and wherein a content of the second transition metal is determined in a range of 0.1% to 20% by weight based on a weight of alumina and the second transition metal is in a form of being loaded on alumina, and a molar ratio of the first transition metal/the second transition metal is in a range of 0.01 to 400.

3. The composite oxide catalyst according to claim 2, wherein the second transition metal is cerium (Ce) and/or zirconium (Zr).

4. The composite oxide catalyst according to claim 2, wherein the first transition metal, the second transition metal, the hydrogen active metal, and the doping metal are gallium, cerium, platinum, and potassium, respectively.

5. The composite oxide catalyst according to claim 1, wherein the hydrogen active metal is at least one selected from the group consisting of Co, Ni, Cu, Ru, Rh, Pd, Ag, Ir, Pt, and Au.

6. The composite oxide catalyst according to claim 1, wherein a content of the hydrogen active metal is determined in a range of 0.03% to 0.09% by weight based on a weight of alumina.

7. The composite oxide catalyst according to claim 1, wherein the doping metal is at least one selected from the group consisting of K, Cs, Mg, and Ca.

8. The composite oxide catalyst according to claim 1, wherein the amount of acid sites of the dehydrogenation catalyst is in a range of 50 to 700 µmol/g as measured by $NH_3$ temperature programmed desorption.

9. A process for preparing 1,3-butadiene, from C4 hydrocarbons, which comprises:

providing a feedstock containing C4 hydrocarbons having a single bond or one double bond;

subjecting the C4 hydrocarbons in the feedstock to dehydrogenation in presence of the composite oxide catalyst according to claim 1 to form a product containing 1,3-butadiene in an increased content; and recovering 1,3-butadiene from the product.

10. The process for preparing 1,3-butadiene according to claim 9, wherein the dehydrogenation is conducted at a temperature of 300° C. to 800° C.

11. The process for preparing 1,3-butadiene according to claim 9, wherein a content of C4 hydrocarbons in the feedstock is at least 10 mol %, a content of hydrocarbons having less than 4 carbon atoms in the feedstock is less than 90 mol %, and a content of hydrocarbons having more than 4 carbon atoms in the feedstock is less than 90 mol %.

12. The process for preparing 1,3-butadiene according to claim 11, wherein a content of C4 paraffins among the C4 hydrocarbons is at least 10 mol %.

13. A process for preparing a composite oxide catalyst for preparing 1,3-butadiene from C4 hydrocarbons via dehydrogenation, which comprises:

a) providing a precursor of at least one first transition metal selected from the group consisting of gallium, vanadium, chromium, manganese, molybdenum, and zinc;

b) providing a precursor of at least one hydrogen active metal selected from the group consisting of elements belonging to groups 8, 9, 10, and 11 of the periodic table;

c) providing a precursor of at least one doping metal selected from the group consisting of elements belonging to groups 1 and 2 of the periodic table;

d) providing a precursor of alumina;

e) mixing the precursor of first transition metal, the precursor of hydrogen active metal, the precursor of doping metal, and the precursor of alumina in one pot to form a one-pot precursor mixture; and f) reacting the one-pot precursor mixture by a sol-gel method to synthesize a catalyst, and g) drying the synthesized catalyst, followed by subjecting to calcination to prepare a catalyst in a composite oxide form;

wherein a content of the first transition metal is determined in a range of 0.1% to 20% by weight based on a weight of alumina, a content of the hydrogen active metal is determined at 0.09% by weight or less based on a weight of alumina, a content of the doping metal is determined in a range of 0.01% to 5% by weight based on a weight of alumina, the first transition metal and the doping metal are each contained in alumina in a solid solution form and the hydrogen active metal is surrounded by alumina containing the first transition metal and doping metal, whereby the doping metal is distributed in the acid sites of alumina to result in a controlled amount of acid sites, a molar ratio of the first transition metal/hydrogen active metal is controlled in a range of 35 to 3000, and a molar ratio of the first transition metal/doping metal is controlled in a range of 0.5 to 10.

14. The process for preparing a composite oxide catalyst according to claim 13, wherein the process further comprises mixing a precursor of at least one second transition metal selected from the group consisting of cerium and zirconium in the one pot, and wherein a content of the second transition metal is determined in a range of 0.1% to 20% by weight based on a weight of alumina in the dehydrogenation catalyst.

15. The process for preparing a composite oxide catalyst according to claim 14, wherein the first transition metal precursor and the second transition metal precursor are each at least one selected from the group consisting of a nitrate, a sulfate, an acetate, a formate, and a halide.

16. The process for preparing a composite oxide catalyst according to claim 13, wherein the drying is performed at 50° C. to 200° C. and the calcination is performed in an oxygen-containing atmosphere at a temperature of 350° C. to 1000° C.

17. The process for preparing a composite oxide catalyst according to claim 13, wherein the one-pot precursor mixture is in a form of a precursor solution dissolved in a solvent, and wherein the solvent is an aqueous medium.

18. The process for preparing a composite oxide catalyst according to claim 13, wherein the precursor of alumina is at least one selected from the group consisting of aluminum acetate, aluminum acetylacetonate, aluminum t-butoxide, aluminum sec-butoxide, aluminum pentoxide, aluminum ethoxide, aluminum isopropoxide, aluminum tributoxide, aluminum fluoride, aluminum chloride, aluminum bromide, aluminum iodide, aluminum sulfate, aluminum nitrate, and any hydrate thereof.

19. The process for preparing a composite oxide catalyst according to claim 13, wherein the precursor of hydrogen active metal is a platinum precursor and is at least one selected from the group consisting of a hydride, a fluoride, a chloride, a bromide, an iodide, an oxide, a sulfide, a carbonyl, and a complex.

\* \* \* \* \*